(12) United States Patent
Fang et al.

(10) Patent No.: US 9,717,753 B2
(45) Date of Patent: Aug. 1, 2017

(54) METHOD FOR REDUCING ARTIFICIAL JOINT REDUCTIONS

(71) Applicant: National Taipei University of Technology, Taipei (TW)

(72) Inventors: Hsu-Wei Fang, Taipei (TW); Shu-Wen Chen, Huwei Township, Yunlin County (TW); Yi-Ling Huang, Tainan (TW)

(73) Assignee: National Taipei University of Technology, Taipei (TW)

( * ) Notice: Subject to any disclaimer, the term of this patent is extended or adjusted under 35 U.S.C. 154(b) by 185 days.

(21) Appl. No.: 14/541,291

(22) Filed: Nov. 14, 2014

(65) Prior Publication Data

US 2015/0328252 A1 Nov. 19, 2015

(30) Foreign Application Priority Data

May 15, 2014 (TW) .............................. 103117191 A

(51) Int. Cl.
*A61K 31/734* (2006.01)

(52) U.S. Cl.
CPC .................................. *A61K 31/734* (2013.01)

(58) Field of Classification Search
None
See application file for complete search history.

(56) References Cited

U.S. PATENT DOCUMENTS

2010/0048506 A1* 2/2010 Iwasaki ................ A61K 31/715
514/54

OTHER PUBLICATIONS

Lee, Injectable Lubricants for Prosthetic Joints, Abstract # 262, 2013 Society for Biomaterials.*
Smith, Journal of the Mechanical Behavior of Biomedical Materials 32 (2014) 177-184.*

* cited by examiner

*Primary Examiner* — Layla Berry
(74) *Attorney, Agent, or Firm* — Juan Carlos A. Marquez; Marquez IP Law Office, PLLC

(57) ABSTRACT

The present invention provides a lubricating composition comprising an alginic acid or a salt or ester thereof, which is effective in reducing frictions in artificial joints and wear of artificial joint implants. Also provided is a method for lubricating artificial joints comprising administering said composition to a synovial cavity of a subject. In another aspect, the present invention provides use of an alginic acid or a salt or ester thereof in manufacturing a lubricating composition.

3 Claims, 5 Drawing Sheets

METHOD FOR REDUCING ARTIFICIAL JOINT REDUCTIONS

RELATED APPLICATION

This application claims the benefit of Taiwan Patent Application No. 103117191, filed on May 15, 2014, the entire content of which is incorporated herein by reference.

STATEMENT REGARDING PRIOR DISCLOSURES BY THE INVENTOR OR A JOINT INVENTOR

A prior presentation, Shu-Wen Chen, Yi-Ling Huang and Hsu-Wei Fang, "Investigating the Characteristics of Biomolecular Additives on the Tribological Behavior of Artificial Joint Materials," was made on Nov. 15, 2013, during Annual Symposium on Biomedical Engineering and Technology.

FIELD OF THE INVENTION

The invention relates to a method for reducing frictions of artificial joints as well as wear caused by the frictions, and thus prevents osteolysis and artificial joint loosening.

BACKGROUND OF THE INVENTION

A synovial membrane of a synovial joint secretes synovial fluid into synovial cavity to absorb and reduce the impact and friction of joints caused by body movement. The synovial fluid can also serve as a medium for nutrients and metabolic waste transportation. Synovial fluid is a composition of a variety of structural biomolecules including polysaccharides, glycoproteins, and proteoglycans as well as functional enzymes such as protease and collagenase. In previous studies, it was found that albumin and hyaluronic acid may be critical molecules that associate with the tribological properties of artificial joints.

Young people often have joint injuries caused by loose ligaments, bacterial infections, gout or other factors. In elders' joints, wear of cartilage and constant collision between the bones result in degenerative osteoarthritis (OA or degenerative arthritis) and pain. When the pain affects motor ability, physical therapy or medications can be used in early stage. If a patient's symptom cannot be alleviated, eventually artificial joint arthroplasty needs to be performed to replace the worn joint so as to maintain motor ability.

The candidate materials commonly used in artificial joints and implants include polymers, metals and ceramics, among which ultra-high molecular-weight polyethylene (UHMWPE) and cobalt-chromium-molybdenum alloy (Co—Cr—Mo Alloy) are quite well known and widely used. However, an artificial joint is not a perfect substitute for an original joint, especially in view of that wear debris caused by friction is inevitable for an artificial joint. Wear debris particles can induce immune responses in the body, and more seriously, it can further lead to osteolysis. If not treated effectively, osteolysis will accelerate artificial joint loosening, which in turn reduces the life of artificial joints. Wear rate of an artificial joint primarily relates to the degree and frequency of a patient's motion, friction coefficient of the artificial joint material and how long the artificial joint has been used. Even though UHMWPE is a tough material with a lower wear rate, its debris is still a threat to a patient's health and life of the implant.

So far, there is still a need for a more effective lubricant to reduce friction and wear debris.

BREIF SUMMARY OF THE INVENTION

It was unexpectedly found in the present invention that alginic acid is very suitable to be used in an artificial joint lubricant to effectively reduce friction coefficient of artificial joints.

Accordingly, in one aspect, the present invention provides a lubricating composition comprising alginic acid or a salt or ester thereof.

In certain embodiments of the present invention, the salt of alginic acid may be calcium alginate, magnesium alginate, or sodium alginate.

The lubricating composition of the present invention may further comprise albumin which is naturally abundant in synovial fluid.

In one embodiment of the invention, the lubricating composition of the present invention further comprises a sulfated polysaccharide, for example, carrageenan, which can further reduce the friction coefficient of the lubricating composition.

Alginic acid or a salt or ester thereof included in a lubricating composition of the present invention is preferably in a concentration of 0.25-15 mg/mL, and more preferably in a concentration of 0.5-12.5 mg/mL.

According to one embodiment of the present invention, alginic acid or a salt or ester thereof, and the sulfated polysaccharide in the lubricating composition are present in a weight ratio of 1:1.

In another aspect, the present invention provides a method for reducing friction of an artificial joint in a subject in need thereof, which comprises administering a lubricating composition of the present invention to a synovialcavity of the subject.

BRIEF DESCRIPTION OF THE DRAWINGS

The invention and the following descriptions can be better understood with reference to the drawings. To illustrate the invention, the embodiments shown in the drawings are merely preferred embodiments instead of limitations.

DETAILED DESCRIPTION OF THE INVENTION

Figure 1:
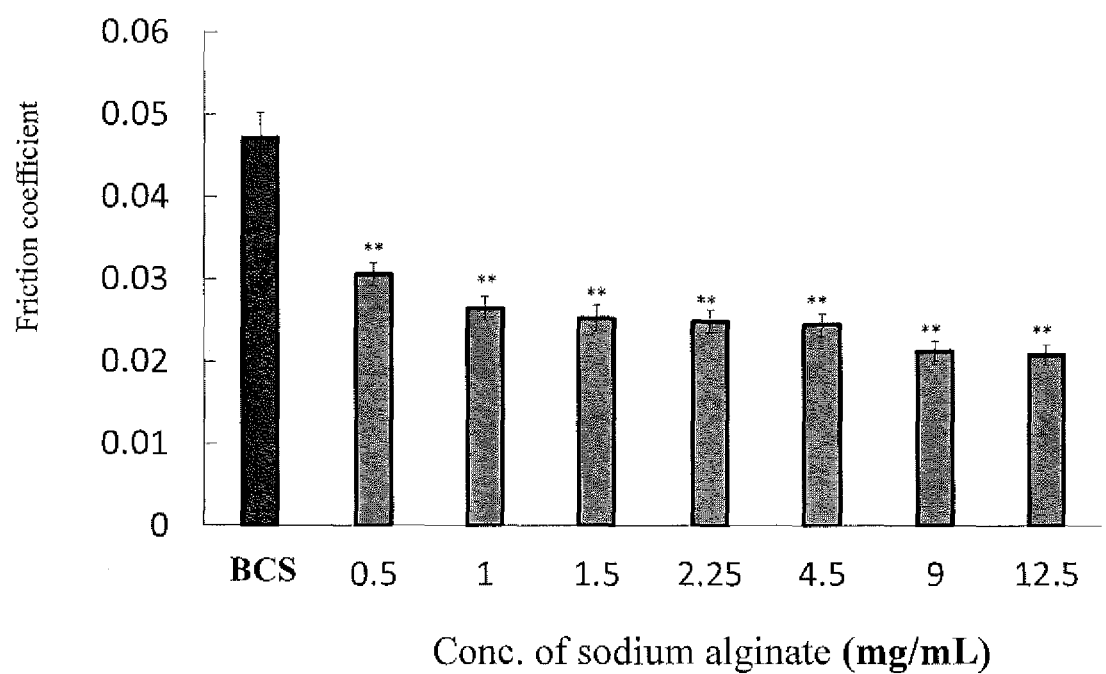
FIG. 1 shows friction coefficients of bovine calf serum (BCS) which adds sodium alginate of different concentrations.
Figure 2:
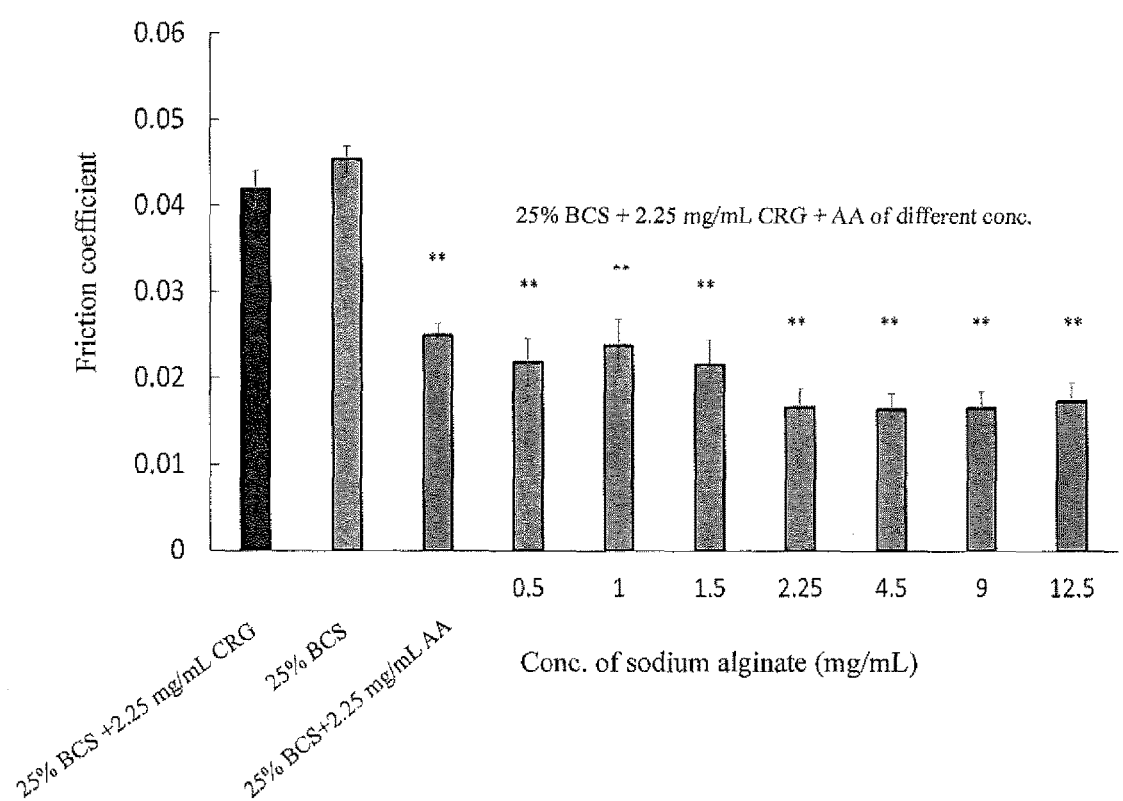
FIG. 2 shows friction coefficients of bovine calf serum (BCS) only, bovine calf serum (BCS) adding carrageenan (CRG), and bovine calf serum (BCS) adding sodium alginate (AA) of different concentrations.

Unless defined otherwise, all technical and scientific terms used herein have the same meaning as commonly understood to one of ordinary skill in the art to which this invention belongs.

In this specification and the appended claims, the singular forms "a," "an," and "the" include plural reference unless the context clearly dictates otherwise. Thus, for example, a sample includes a plurality of such samples and equivalents known in this art.

As used herein, the term "salt" refers to a compound resulting from a neutralization reaction of an acid and a base. Preferably, a salt is formed by an acid anion or non-metallic ion in combination with a metal ion such as sodium or magnesium.

As used herein, the term "ester" refers to a compound generated by esterification of an inorganic acid or organic acid in which at least one hydroxyl group is replaced by an alkoxy group. Preferably, an ester can be generated by a carboxylic acid or inorganic oxoacid in combination with an alcohol.

Alginic acid, also called algin or alginate is widely distributed in cell walls of brown algae and bacterial capsules. The first step in alginate production is an ion-exchange with protons by extracting milled algal tissues. Subsequently, an alkaline solution is added for neutralization. Sodium alginate (Na-alginate) is most commonly manufactured. Fucoidan currently used in commercial purposes is also derived from natural algae.

Carrageenan is a natural sulfated polysaccharide and is water-soluble. It belongs to a family of linear sulfated galactose. The source is red algae, such as *Chondruscrispus*. Carrageenan can be fractionated into lambda-carrageenan and kappa-carrageenan by KCl extraction, Preferably, lambda-carrageenan is used in the present invention.

As used herein, the "synovial cavity" refers to a cavity of a movable joint between two bones, in which synovial fluid is filled. The synovial fluid is a buffer region and provides lubrication when the bones move.

In one aspect, the present invention provides a method for reducing friction of an artificial joint in a subject in need thereof comprising administering a lubricating composition comprising alginic acid or a salt or ester thereof to a synovial cavity of the subject, and thereby lubricating the artificial joint.

In another aspect, the present invention provides use of alginic acid or a salt or ester thereof for the preparation of a composition for lubricating an artificial joint.

The salts include but are not limited to calcium alginate, magnesium alginate, and sodium alginate.

According to one embodiment of the present invention, the concentration of alginic acid or a salt or ester thereof included in the lubricating composition is preferably 0.25-15 mg/mL, more preferably 0.4-15 mg/mL, further more preferably 0.5-12.5 mg/mL.

The lubricating composition of the present invention may further comprise albumin which is naturally abundant in synovial fluid. The amount of albumin can be adjusted based on a natural synovial fluid.

In addition, the lubricating composition of the present invention may further comprise a sulfated polysaccharide to further reduce the friction coefficient. In certain embodiments of the present invention, the sulfated polysaccharide is carrageenan.

According to one embodiment of the present invention, the alginic acid or a salt or ester thereof, and the sulfated polysaccharide are present in a weight/concentration ratio of 1:1.

In another embodiment, the concentration of the alginic acid or a salt or ester thereof in the composition is 4-5 mg/mL, and concentration of the sulfated polysaccharide is 4-5 mg/mL.

With reference to the following examples, the subject invention is described more specifically for illustrative purposes rather than limitations.

EXAMPLES

Example 1

Friction Testing

Effects of different biomolecule additives on the friction coefficients between friction pairs were examined using Universal Micro-Tribometer (UMT).

The UMT was set at the configurations of pin-on-disc (POC) and rotary motion in the test to allow Co—Cr—Mo Alloy and UHMWPE to friction each other as a friction pair. Different lubricating fluids were added between the surfaces in contact of the friction pair to access their effects on the friction coefficients of artificial joint materials.

Since UHMWPE is absorbent, it was immersed in deionized water until saturation before the test. Co—Cr—Mo Alloy was maintaining smooth by polishing. Other fixtures, containers and devices were washed by deionized water and sterilized.

Feedback control of load was achieved through the adjustment by a servo valve, based on a response generated by comparing a deviation between a feedback signal and input signal. Under a fixed load, friction force due to relative motion of material surfaces was recorded by a force sensor every 0.3 second. Experimental data such as normal force, friction force and friction coefficient were output by a computer. Data of the last 30 seconds were averaged and subjected to analysis of variance (ANOVA). $P<0.05$ indicates statistically significant difference and $P<0.001$ indicates high significance.

Example 2

Tribological Properties of Single Biomolecule Additive

While developing a proper lubricant, a basal solution was used to simulate the environment of human body. According to international test standard, bovine calf serum is often used as a lubricant base in view of its similarity to human synovial fluid and its availability. In the present invention, 50% bovine calf serum was used as a lubricant base, which was further mixed with a biomolecule additive solution in an 1:1 ratio so that final concentration of bovine calf serum was 25% (v/v). Total protein content was less than 17 mg/mL in accordance with the requirements for artificial joint simulator.

Different biomolecule additives mg/mL were added to bovine calf serum at a concentration of 2.25, 4.5, 9, or 12.5 to evaluate their lubricating effects on the artificial joint material UHMWPE-CoCrMo friction pair.

Figure 3:
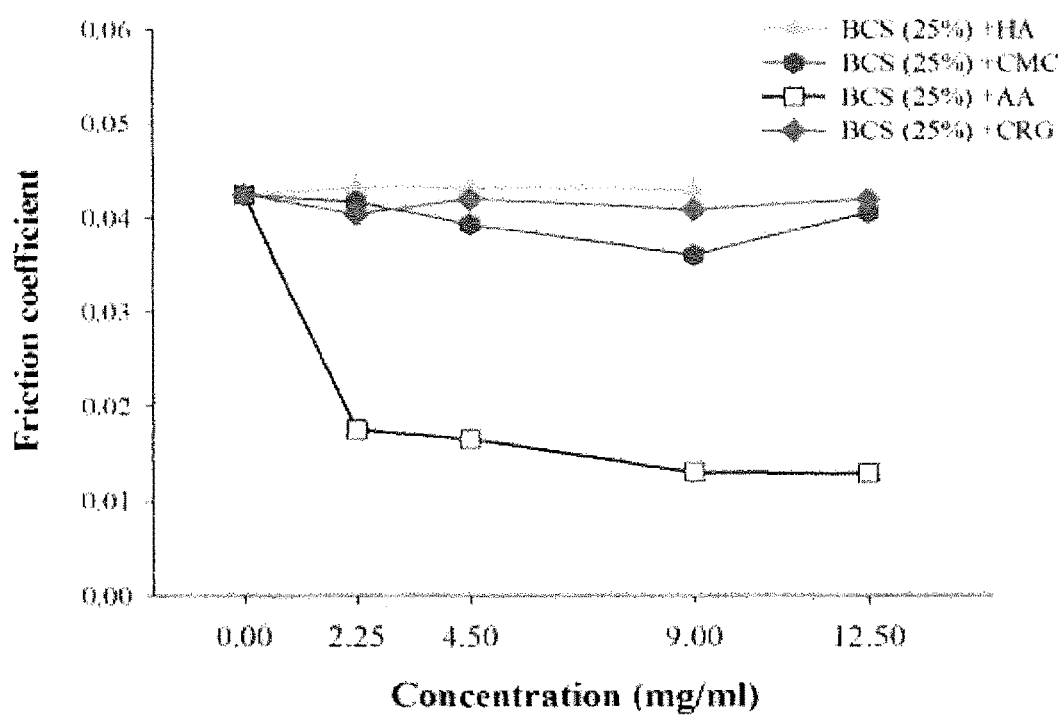
FIG. 3 shows friction coefficients of 25% bovine calf serum (BCS) which adds different concentrations of hyaluronic acid (HA), carboxymethyl cellulose (CMC), sodium alginate (AA) or carrageenan (CRG).

As shown in FIG. 3, a bovine calf serum comprising sodium alginate reduced the friction coefficient with a statistically significant difference. The hyaluronic acid was not effective in reducing friction coefficient. Bovine calf serum comprising carboxymethyl cellulose or carrageenan only slightly reduced the friction coefficients.

In addition, it was observed that the friction coefficients decreased with a statistically significant difference while the concentration of sodium alginate was increased. Similar behavior was observed while increasing the concentration of carboxymethyl cellulose. However, the concentrations of hyaluronic acid and carrageenan did not significantly influence the friction coefficients.

Example 3

Tribological Properties of Multiple Biomolecule Additives

To further investigate the lubricating effects of sodium alginate, multiple biomolecule additives were added to bovine calf serum and the friction coefficients were examined.

Figure 4:
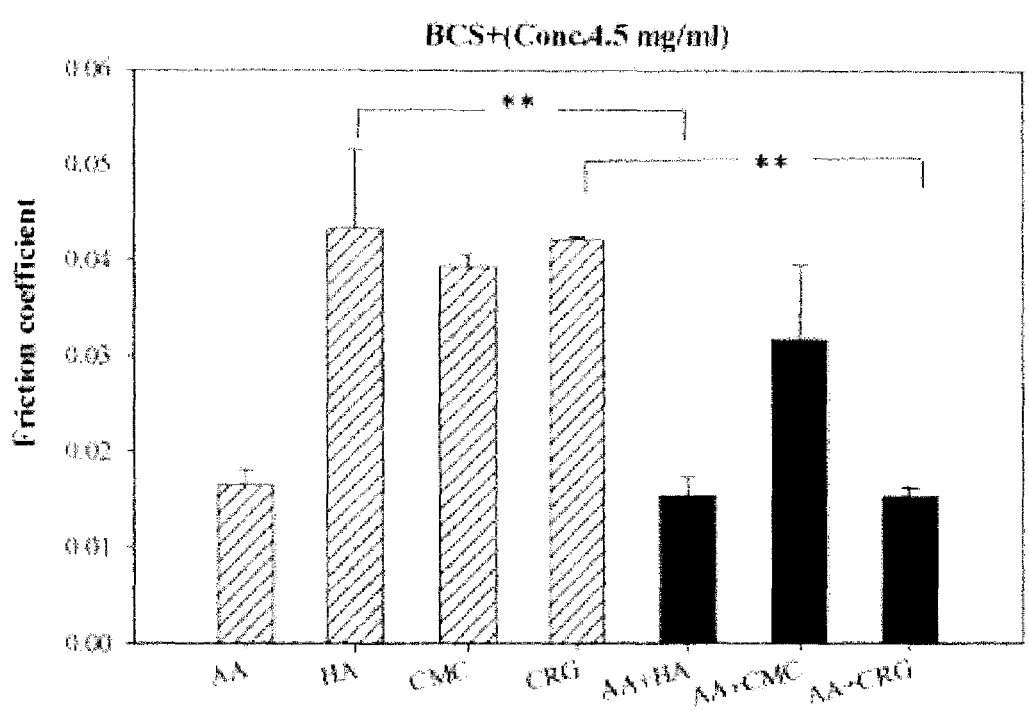
FIG. 4 shows friction coefficients of bovine calf serum (BCS) containing 4.5 mg/mL single/multiple biomolecule additive(s).

For one test, the concentration of total biomolecule additives in bovine calf serum was 4.5 mg/mL in each group. As shown in FIG. 4, compared with bovine calf serum supplemented with hyaluronic acid only (bovine calf serum:hyaluronic acid=1:1), bovine calf serum supplemented with hyaluronic acid and sodium alginate (bovine calf serum:hyaluronic acid:sodium alginate=1:0.5:0.5) demonstrated significant effects in decreasing the friction coefficients ($P<0.05$). In addition, bovine calf serum supplemented with carrageenan and sodium alginate also showed significant effects in decreasing the friction coefficients as compared to bovine calf serum supplemented with carrageenan only.

Figure 5:
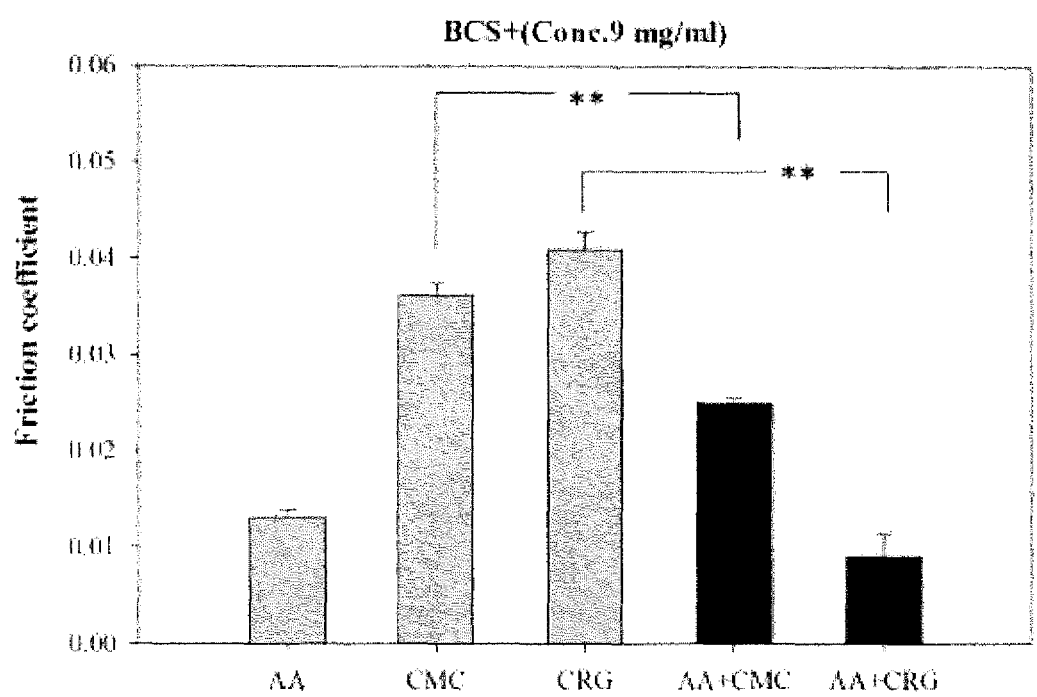
FIG. 5 shows friction coefficients of bovine calf serum (BCS) containing 9 mg/mL single/multiple biomolecule additive(s).

In another test, the concentration of total biomolecule additives in bovine calf serum was 9 mg/mL. As can be seen in FIG. 5, compared with bovine calf serum supplemented with one biomolecule additive only, bovine calf serum supplemented with two biomolecule additives demonstrated significant effects in decreasing the friction coefficients. For example, bovine calf serum supplemented with carboxymethyl cellulose and sodium alginate showed significant effects in decreasing friction coefficients as compared to bovine calf serum supplemented with carboxymethyl cellulose only ($P<0.05$).

We claim:

1. A method for reducing friction of an artificial joint in a subject in need thereof, comprising administering a lubricating composition comprising, as the sole active ingredients (i) alginic acid, or a salt or ester thereof and (ii) albumin, to a synovial cavity of the subject.

2. The method of claim 1, wherein the composition comprises alginic acid, or a salt or ester thereof in a concentration of 0.25-15 mg/mL.

3. The method of claim 1, wherein the composition comprises alginic acid, or a salt or ester thereof in a concentration of 0.5-12.5 mg/mL.

* * * * *